(12) United States Patent
Neergaard

(10) Patent No.: US 11,723,918 B2
(45) Date of Patent: *Aug. 15, 2023

(54) SOLID PHARMACEUTICAL TABLET

(71) Applicant: FERTIN PHARMA A/S, Vejle (DK)

(72) Inventor: Jesper Neergaard, Aabenraa (DK)

(73) Assignee: FERTIN PHARMA A/S, Vejle (DK)

(*) Notice: Subject to any disclaimer, the term of this patent is extended or adjusted under 35 U.S.C. 154(b) by 120 days.

This patent is subject to a terminal disclaimer.

(21) Appl. No.: 17/206,226

(22) Filed: Mar. 19, 2021

(65) Prior Publication Data

US 2021/0205355 A1    Jul. 8, 2021

Related U.S. Application Data

(63) Continuation of application No. 15/933,942, filed on Mar. 23, 2018, now Pat. No. 10,980,831.

(51) Int. Cl.
| | |
|---|---|
| *A61K 33/10* | (2006.01) |
| *A61K 9/00* | (2006.01) |
| *A61K 9/20* | (2006.01) |
| *A61K 31/192* | (2006.01) |
| *A61K 9/68* | (2006.01) |
| *A61K 31/167* | (2006.01) |

(52) U.S. Cl.
CPC ............ *A61K 33/10* (2013.01); *A61K 9/0053* (2013.01); *A61K 9/0058* (2013.01); *A61K 9/20* (2013.01); *A61K 9/2009* (2013.01); *A61K 9/2031* (2013.01); *A61K 31/167* (2013.01); *A61K 31/192* (2013.01)

(58) Field of Classification Search
CPC ..... A61K 33/10; A61K 9/0053; A61K 9/0058
See application file for complete search history.

(56) References Cited

U.S. PATENT DOCUMENTS

| | | |
|---|---|---|
| 4,327,076 A | 4/1982 | Puglia et al. |
| 4,753,805 A | 6/1988 | Cherukuri et al. |
| 5,637,313 A | 6/1997 | Chau et al. |
| 7,871,650 B2 | 1/2011 | Sozzi et al. |
| 8,765,178 B2 | 7/2014 | Parikh et al. |
| 8,828,361 B2 | 9/2014 | Andersen |
| 10,933,017 B2 | 3/2021 | Bruun et al. |
| 2010/0215799 A1 | 8/2010 | Cosgrove et al. |

FOREIGN PATENT DOCUMENTS

| | | | |
|---|---|---|---|
| EP | 0236271 | A2 | 9/1987 |
| GB | 2542192 | * | 3/2017 |
| GB | 2542192 | A | 3/2017 |
| JP | S62258317 | A | 11/1987 |
| JP | H03133341 | A | 6/1991 |
| JP | 2002542185 | A | 12/2002 |
| JP | 2005514048 | A | 5/2005 |
| JP | 2008504828 | A | 2/2008 |
| JP | 2010518845 | A | 6/2010 |
| JP | 2017517490 | A | 6/2017 |
| WO | 0062762 | A1 | 10/2000 |
| WO | 03059082 | A1 | 7/2003 |
| WO | 2003059082 | A1 | 7/2003 |
| WO | 2006002622 | A1 | 1/2006 |
| WO | 2008104546 | A1 | 9/2008 |
| WO | 2015070875 | A1 | 5/2015 |
| WO | 2015154780 | A1 | 10/2015 |
| WO | 2017059858 | A1 | 4/2017 |
| WO | 2017191571 | A1 | 11/2017 |

OTHER PUBLICATIONS

PCT: International Search Report of PCT/DK2019/050100 (related application); dated Jun. 25, 2019; 4 pages.
Office Action in JP2020-550793 (JP Counterpart Application), dated Jan. 17, 2023, with English machine translation.

* cited by examiner

*Primary Examiner* — Genevieve S Alley

(57) ABSTRACT

The invention relates to a solid pharmaceutical tablet for oral delivery, the tablet comprising calcium carbonate in an amount of more than 30% by weight of the tablet and organic water-insoluble components in an amount of more than 20% by weight of the tablet, wherein the tablet is designed to be masticated into a coherent residual containing the organic water-insoluble components, and wherein the tablet is adapted to release more than 80% of the calcium carbonate within 5 minutes of mastication.

20 Claims, No Drawings

SOLID PHARMACEUTICAL TABLET

CROSS-REFERENCE TO RELATED APPLICATIONS

This application is a continuation of U.S. application Ser. No. 15/933,942, filed Mar. 23, 2018, and entitled A SOLID PHARMACEUTICAL TABLET, which is incorporated by reference in its entirety.

TECHNICAL FIELD

The invention relates to a solid pharmaceutical tablet for oral delivery and a method of releasing an active pharmaceutical ingredient, such as calcium carbonate, from a solid pharmaceutical tablet.

BACKGROUND

Tablets containing calcium carbonate are well-known. Such tablets are designed and used e.g. for gastrointestinal benefit. A challenge with such known tablets is that such tablets are typically most suitable for swallowing as such tablets include significant amounts of calcium carbonate. These significant amounts of calcium carbonate would be expected to lead to oral displeasure in terms of texture or mouthfeel if the tablets were to be administered as chewable tablets.

SUMMARY

The invention relates to a solid pharmaceutical tablet for oral delivery, the tablet comprising calcium carbonate in an amount of more than 30% by weight of the tablet and organic water-insoluble components in an amount of more than 20% by weight of the tablet, wherein the tablet is designed to be masticated into a coherent residual containing the organic water-insoluble components, and wherein the tablet is adapted to release more than 80% of the calcium carbonate within 5 minutes of mastication.

According to an embodiment of the invention, a solid pharmaceutical tablet has been provided which enables an advantageous release of calcium carbonate into the oral cavity of a user. The release, obtained through use of organic water insoluble components, which may be masticated into a coherent residual containing the organic water-insoluble components, is significant and the inventive tablet both provides a solution where a user may avoid swallowing the tablet while still obtaining a significant amount of calcium carbonate. At the same time, it is also possible to obtain the desired release without inferring negative texture feeling by a user, which would usually be expected when releasing such high amounts of calcium carbonate into the mouth of a user by means of a chewable product.

Thus, the obtained texture is, un-expectedly, far from the chalkiness feeling a user may have when chewing a tablet comprising large amounts of calcium carbonate or when introducing powdered calcium carbonate into the oral cavity.

In other words, the inventive tablet is an attractive delivery vehicle for calcium carbonate specifically targeting challenges with delivery and release of calcium carbonate from a tablet.

The present inventive tablet may thus be regarded as a new delivery vehicle for calcium carbonate, which is in particular advantageous when using calcium carbonate as an active pharmaceutical ingredient, i.e. an ingredient intended for a specific pharmaceutical effect.

A further advantage, which may be obtained according to the provisions of the invention, is a reduction of the risk of overdose. A user masticating the inventive tablet may thus typically prolong mastication of the tablet due to the presence of the coherent residual, thereby at least prolonging the time until a new tablet is applied. This is not unimportant, as sustained overdose of calcium carbonate over time can lead to hypercalcaemia. Symptoms of hypercalcaemia may include anorexia, thirst, nausea, vomiting, constipation, abdominal pain, muscle weakness, fatigue, mental disturbances, polydipsia, polyuria, bone pain, nephrocalcinosis, nephrolithiasis and in severe cases, cardiac arrhythmias. Extreme hypercalcaemia may result in coma and death. Persistently high calcium levels may lead to irreversible renal damage and soft tissue calcification.

The applied calcium carbonate may advantageously be a commercially available DC-grade (DC: Direct compressible) of calcium carbonate.

In an embodiment of the invention, the tablet comprises calcium carbonate in an amount of 30 to 60% by weight of the tablet.

According to an advantageous embodiment the tablet may comprise significant amounts of calcium carbonate. The inventive tablet may thus comprise calcium carbonate in an amount of 30 to 60% by weight of the tablet.

In an embodiment of the invention, the tablet comprises calcium carbonate in an amount of 35 to 55% by weight of the tablet.

In an embodiment of the invention, the tablet comprises calcium carbonate in an amount of 40 to 50% by weight of the tablet.

According to an advantageous embodiment the tablet may comprise significant amounts of calcium carbonate. The inventive tablet may advantageously comprise around 45% by weight of the tablet thereby facilitating release of an effective amount of pharmaceutically active ingredient, i.e. the calcium carbonate, without either compromising the user's ability or desire to invoke the release.

In an embodiment of the invention, the tablet is adapted to release more than 85% of the calcium carbonate within 5 minutes of mastication of the tablet.

The tablet may thus be designed to release a significant amount of the calcium carbonate, e.g. 85% of the carbonate contained within the tablet product within a very short time period. The fast though still delayed release may be regarded as a key for obtaining the desired pharmaceutical effect, as an inferior textural sensation during mastication would typically demotivate the user for continued mastication and thereby reduce the desired pharmaceutical effect which should be obtained through released calcium carbonate.

The referred release of calcium carbonate may be determined in two different ways within the scope of the invention, In Vivo relase or In vitro release.

In vivo release: 6 assessors were instructed to masticate each sample with 60 chews per minute for a total mastication time of 3 to 10 minutes.

The assessors were instructed not to eat or drink anything but water for the last 30 minutes before the test. Prior to test start the assessors rinsed their mouths with water.

For each sample tested, the assessors chewed a tablet for 3 minutes, another tablet for 5 minutes and yet another tablet for 10 minutes to produce tablet residuals for each time point. This was repeated once to obtain replicates for each assessor at each time point in the test In vitro release: The release of calcium carbonate in this example was determined in vitro. The measurements were carried out according to the procedure set forth in the Ph.

Eur. 6th ed. 2.9.25, in a phosphate buffer with pH=7.4, a mastication rate of 60 chew per minute, and with the temperature of the medium set at 37° C. The mastication process was interrupted every minute to replace the phosphate buffer thereby preventing saturation of the buffer and simulating swallowing in the in vivo mastication process.

For each sample one tablet was masticated at specified time intervals 3, 5 and 10 minutes to produce tablet residuals for each time point. This was repeated 6 times to obtain 6 replicates for each time point in the test.

Calcium carbonate content of the residuals after mastication, in vitro or in vivo, can be determined by standard Atomic absorption spectroscopy (AAS). For analysis, a tablet residual was dissolved in a mixture of hydrochloric acid (HCl) and toluene. Following proper dilution and filtration, the acidic phase was passed through the AAS device analyzing for Ca (at a wave length of 442.7 nm).

The release was then calculated by comparing the Ca content of the residual after mastication with the Ca content of the non-masticated tablet.

Alternatively, standard titration techniques may be used to determine the calcium carbonate content before and after mastication.

In an embodiment of the invention, the tablet is adapted to release more than 90% of the calcium carbonate within 5 minutes of mastication of the tablet.

In an embodiment of the invention, the tablet is adapted to release more than 60% of the calcium carbonate within 3 minutes of mastication of the tablet.

In an embodiment of the invention, the tablet is composed of a pressed mixture of particles and/or granules.

According to an advantageous embodiment of the invention, the tablet may be formed by a pressed mixture of particles and/or granules. This is in particular relevant when the particles and granules are of a different nature in terms of content and e.g. size, as these may both be pressed together for the purpose of forming a mechanically stable tablet and even more importantly, be used as interacting exhibitors of calcium carbonate.

A granule in the present context is understood as an agglomerate of powder/particles. A granule is thus a structure produced through granulation. This granulation process by itself is well-known within the art.

In an embodiment of the invention, the calcium carbonate and the organic water-insoluble components are contained in different particles and/or granules before tableting.

The above-mentioned effect of interacting exhibitors in relation to calcium carbonate may be advantageously obtained when calcium carbonate of the tablet is contained in other particles that the particles comprising the organic water-insoluble components. During mastication, such a configuration of an exhibiting tablet matrix may both invoke that calcium carbonate is immediately released but also that some of the immediately released calcium carbonate is masticated mechanically into the coherent residual and then later again at least partly released from the coherent residual.

In an embodiment of the invention, more than 80% of the calcium carbonate is contained in particles and/or granules different from the particles and/or granules comprising the organic water-insoluble components before tableting.

The calcium carbonate may thus be contained in different types of particles and/or granules, thereby obtaining a hybrid type of release, while still maintaining an overall very fast release and relatively complete release of calcium carbonate. A relatively complete release of calcium carbonate in the present context refers to that only a minor fraction of the originally contained calcium carbonate is still contained in the coherent residual at the given point of time after initiation of mastication.

In an embodiment of the invention, the tablet comprises organic water-insoluble components in an amount of 20 to 50% by weight of the tablet.

The organic water-insoluble components may constitute a significant amount of the tablet, while still maintaining the desired fast release of calcium carbonate and while maintaining an attractive mouthfeel.

The invention furthermore relates to a solid pharmaceutical tablet for oral delivery, the tablet comprising an active pharmaceutical ingredient in an amount of more than 30% by weight of the tablet and organic water-insoluble components in an amount of more than 20% by weight of the tablet, wherein the tablet is designed to be masticated into a coherent residual containing the organic water-insoluble components, and wherein the tablet is adapted to release more than 80% of the active pharmaceutical ingredient within 5 minutes of mastication.

According to an advantageous embodiment of the invention, the solid pharmaceutical tablet delivers an active pharmaceutical ingredient, such as calcium carbonate. The active pharmaceutical ingredient may be released from the tablet with little or no oral displeasure and the pharmaceutical ingredient may therefore have a greater chance of success in terms of the intended result or treatment, simply due to the fact that a user of the tablet will be motivated for chewing the tablet. The desired pharmaceutical effect would of course be reduced if a user would tend to refrain from either using the tablet or refrain from masticating the tablet due to e.g. displeasure or bad taste.

In an embodiment of the invention, the active pharmaceutical ingredient is an ingredient that provides an oral and/or gastrointestinal benefit.

In an embodiment of the invention, the active pharmaceutical ingredient provides an acid neutralizing action.

In an embodiment of the invention, the active pharmaceutical ingredient forms a complex with an auxiliary ingredient after oral administration.

Administration in the present context is understood as the process of using a drug in order to cause physiological changes, e.g. as prescribed by a doctor to treat or prevent a medical condition.

In an embodiment of the invention, the tablet comprises calcium carbonate in an amount of more than 15% by weight of the tablet and organic water-insoluble components in an amount of more than 25% by weight of the tablet, wherein the tablet is designed to be masticated into a coherent residual containing the organic water-insoluble components, and wherein the tablet is adapted to release more than 80% of the calcium carbonate within 5 minutes of mastication.

The invention furthermore relates to a method of releasing calcium carbonate from a solid pharmaceutical tablet, the method comprising: a) providing a tablet comprising calcium carbonate in an amount of more than 30% by weight of the tablet and organic water-insoluble components in an amount of more than 20% by weight of the tablet, b) masticating the tablet into a coherent residual containing the organic water-insoluble components, c) generating fluid in the oral cavity, d) releasing more than 80% of the calcium carbonate to the fluid in the oral cavity within 5 minutes of mastication.

In an embodiment of the invention, the masticating of the tablet provides a teeth cleaning benefit.

The tablet may thus provide a teeth-cleaning benefit from both the released calcium carbonate, but also due to the friction between the teeth and the coherent residual during mastication.

In an embodiment of the invention, the masticating tablet does not provide a chalkiness taste sensation.

The inventive tablet, which is an excellent oral exhibitor of calcium carbonate, may advantageously be used as a "two-way" delivery system, which releases calcium carbonate from the tablet, and at the same time releases calcium carbonate for incorporation into the coherent residual during mastication, thereby providing a physical "release-buffer", which may be regarded as a facilitator for the advantageous in-use texture of the product.

It was a surprise to the inventor of the present invention that it was possible to obtain a release of calcium carbonate according to the invention without providing a chalkiness taste sensation during mastication. A relatively high release of calcium carbonate according to the invention would be expected to result in a more pronounced chalkiness sensation during mastication. This is highly surprising in view of conventional thinking. In fact, the high release of calcium carbonate according to the invention is in itself highly surprising given the content of organic water-insoluble components in the formulation according to the invention.

The pressing force applied during tableting of particles/granules into a tablet may influence the chalkiness and the undesired chalkiness may be reduced when applying compression force or larger than 25 kN.

In an embodiment of the invention, less than 15% calcium carbonate is present in the coherent residual containing the organic water-insoluble components after 5 minutes of mastication.

In an embodiment of the invention, less than 15% calcium carbonate is masticated into the coherent residual containing the organic water-insoluble components after 5 minutes of mastication.

The inventive tablet, which is an excellent oral exhibitor of calcium carbonate, may advantageously be used as a two-way delivery system, which both releases calcium carbonate from the tablet, and at the same time releases calcium carbonate for incorporation into the coherent residual during mastication, thereby providing a physical "release-buffer", which may be regarded as a facilitator for the advantageous in-use texture of the product.

In an embodiment of the invention, the release of calcium carbonate provides an oral and/or gastrointestinal benefit.

DETAILED DESCRIPTION

In some embodiments of the invention, the tablet comprises calcium carbonate and organic water-insoluble components. In some embodiments of the invention, the tablet comprises an active pharmaceutical ingredient, such as calcium carbonate, and organic water-insoluble components. The organic water-insoluble components according to various embodiments are described in the following.

Water-insoluble components in the present context typically refer to elastomer, natural or synthetic resins or other water-insoluble components such as water-insoluble softener.

The term "organic" is used in its usual meaning within chemistry, particularly as the subject of compounds and matter within organic chemistry as opposed to inorganic chemistry.

As used herein, the phrase "tablet" refers to a tablet made by tabletting in a tabletting machine by pressing the tablet material to form the tablet. For example, the tablet material may be exposed to a punching means in a tabletting machine, pressing e.g. granules and/or powder to a gathered mass of pressed material.

The tabletting may be performed at a certain pressure, e.g. typically defined as compression force. Different types of tabletting machines are known within the art, such as a rotary press device available by Fette.

As used herein, the phrase "granules" refers to entities made e.g. by granulation, and may typically contain a plurality of particles adhered together.

By the phrase "texture" is meant a qualitative measure of the visco-elastic properties of the tablet and of the overall mouth-feel experienced by the user during the mastication process. Thus, the term "texture" encompasses measurable quantities such as hardness and elasticity as well as more subjective parameters related to the chew-feel experienced by a user.

"Calcium carbonate" in the present context primarily refers to direct compressible (DC) calcium carbonate although minor amounts of non-direct compressible (non-DC) calcium carbonate may be applied within the scope of the invention.

Calcium carbonate may thus be applied as particles, but in the present embodiments, calcium carbonate may typically be applied as a granulate. Calcium carbonate may thus typically be granulated with starch, maltodextrin, Poly Vinyl Pyrrolydone (PVP), gum Arabic/acacia or other suitable binder in order to make the calcium carbonate directly compressible.

The preferred calcium carbonate is thus DC grades, including e.g. CS90 and CM90 from SPI Pharma. Other commercially available DC grades of calcium carbonate may be applied within the scope of the invention, such as Scoralite LL250 DC 97PVP from Scora S.A.S or Calcium Carbonate DC 90S from Lohmann.

In some embodiments of the present invention, the organic water-insoluble components comprise, for example, elastomer in the range of 1-15% by weight of the tablet, natural and/or synthetic resin in the range of 5-35% by weight of the tablet, and further other organic water insoluble components in the range of 5-30% by weight of the tablet.

It is evident, that the overall total amount of these above organic water-insoluble components must be mutually adjusted in order to fit requirements with respect to tablet content of calcium carbonate, sweetener, flavor, etc.

In some embodiments of the present invention, the tablet comprises natural resins in an amount of 0.1 to 30%, such as 1 to 25%, such as 3 to 25% or 5 to 25%, by weight of the tablet.

In some embodiments of the present invention, the tablet comprises natural resins in an amount of at least 10% by weight of the tablet.

In some embodiments of the present invention, the tablet is free of natural resins.

In embodiments of the present invention, the tablet comprises synthetic resins in an amount of 0.1 to 30%, such as 1 to 25%, such as 3 to 25% or 5 to 25%, by weight of the tablet.

In embodiments of the present invention, the tablet comprises elastomer in an amount of at least 2% by weight of the tablet, such as at least 4% by weight of the tablet.

In embodiments of the present invention, the tablet comprises elastomer in an amount of less than 35% by weight of the tablet, such as less than about 25% by weight of the tablet, such as less than 20%, 15% or 10% by weight of the tablet.

In embodiments of the present invention, the tablet comprises one or more flavoring agents, preferably in powdered form, selected from the group consisting of essential oils, essences, extracts, powders, acids, coconut, coffee, chocolate, vanilla, grape fruit, orange, lime, menthol, liquorice, caramel aroma, honey aroma, peanut, walnut, cashew, hazelnut, almonds, pineapple, strawberry, raspberry, apple, pear, peach, apricot, blackberry, cherry, pineapple, plum essence, clove oil, bay oil, anise, thyme, cedar leaf oil, nutmeg, cinnamon, peppermint, wintergreen, spearmint, *eucalyptus*, mint, or any combination thereof.

In embodiments of the present invention, the tablet comprises one or more humectants, such as propylene glycol or glycerol.

In embodiments of the present invention, the tablet is provided with a coating.

In embodiments of the present invention, the tablet has a weight in the range of 0.1 to 10 grams, such as in the range of 0.5 to 4 grams or such as in the range of 1.5 to 2.5 grams.

According to an embodiment of the invention, the tablet may comprise filler. In embodiments of the present invention, the tablet comprises an additional filler in an amount of 0.1 to 40% by weight of the tablet.

Elastomers provide the rubbery, cohesive nature to the tablet, which varies depending on this ingredient's chemical structure and how it may be compounded with other ingredients. Elastomers suitable for use in the tablet of the present invention may include natural or synthetic types.

Elastomer plasticizers vary the firmness of the organic water-insoluble components. Their specificity on elastomer inter-molecular interaction (plasticizing) along with their varying softening points cause varying degrees of finished tablet firmness and compatibility with other ingredients. This may be important when one wants to provide more elastomeric chain exposure to the alkane chains of the waxes. The elastomer plasticizers may typically may resins, such as synthetic resins and/or natural resins.

The elastomers employed in the tablet may vary depending upon various factors such as the desired texture of the coherent residual (i.e. the tablet after mastication) and the other components used in the formulation to make the tablet. The elastomer may be any water-insoluble polymer known in the art. Illustrative examples of suitable polymers in the tablet include both natural and synthetic elastomers. For example, those polymers which are suitable in the tablet include, without limitation, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, and the like, and mixtures thereof.

Natural resins may be used according to the invention and may be natural rosin esters, including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the resin comprises terpene resins, e.g. derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerised rosins, pentaerythritol esters of partially hydrogenated rosins, methyl esters of rosins, partially hydrogenated methyl esters of rosins or pentaerythritol esters of rosins and combinations thereof.

In an embodiment of the invention a synthetic resin may include polyvinyl acetate (PVAc) and/or vinyl acetate-vinyl laurate (VA-VL) copolymers In an embodiment of the invention, the tablet may comprise one or more components selected from the group consisting of bulk sweeteners, flavors, dry-binders, tabletting aids, anti-caking agents, emulsifiers, antioxidants, enhancers, absorption enhancers, high intensity sweeteners, softeners, colors, or any combination thereof.

In an embodiment of the invention, the tablet comprises sweeteners, such as bulk sweeteners, sugar sweeteners, sugar substitute sweeteners, artificial sweeteners, high-intensity sweeteners, or any combination thereof.

Suitable bulk sweeteners include both sugar and non-sugar sweetening components.

Bulk sweeteners typically constitute from about 5 to about 95% by weight of the tablet, more typically about 20 to about 80% by weight such as 30 to 70% or 30 to 60% by weight of the tablet.

Useful sugar sweeteners are saccharide-containing components commonly known in the tablet art including, but not limited to, sucrose, dextrose, maltose, lactose, dextrins, trehalose, D-tagatose, dried invert sugar, fructose, levulose, galactose, corn syrup solids, and the like, alone or in combination.

As an example, sorbitol can be used as a non-sugar sweetener. Other useful non-sugar sweeteners include, but are not limited to, other sugar alcohols such as mannitol, xylitol, maltitol, isomalt, erythritol, lactitol and the like, alone or in combination.

High intensity artificial sweetening agents can also be used alone or in combination with the above sweeteners. For example, high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (such as from about 0.02 to about 8% by weight). When carriers used for encapsulation are included, the usage level of the encapsulated sweetener will be proportionately higher. Combinations of sugar and/or non-sugar sweeteners may be used in the tablet formulation.

A tablet according to the invention may, if desired, include one or more fillers/texturisers including as examples, magnesium, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood or microcrystalline cellulose (MCC), and combinations thereof.

A number of further tablet materials well known within the art may be applied within the scope of the present invention. Such components comprise but are not limited to waxes, fats, softeners, fillers, flavors, anti-oxidants, emulsifiers, colouring agents, binding agents and acidulants The granules or some of the granules may for example consist or largely comprise of organic water-insoluble components and such granules may be manufactured by means of extrusion and under-water pelletizing.

The size of such granules of organic water-insoluble components may according to the present invention be controlled by several factors such as opening sizes, the tablet composition, tablet temperature and pressure drop, if a die plate is used in the extruder. Due to an interaction between the pressurized tablet composition, temperature and friction in the openings of the die device, the average diameter of the produced granules are normally larger than the diameters of the openings in the die device. The relation between the diameters of the openings in the die device and the average diameters of granules produced from a specific tablet composition may be determined by the skilled person on basis of routine experiments.

According to the invention it is also possible to produce granules with different average diameters by making granules with one diameter, and subsequently mix the granules with different average diameters in desired proportions.

Although the openings of a die of an extruder device may have cross-sections of any desired shape, e.g. circular, oval, square etc., it is in some embodiments preferred that the die device comprises openings with substantially circular cross-section and diameters in the range of 0.1 to 1.3 mm. A first set of openings can e.g. have a first diameter in the range of 0.07 to 0.7 mm, such as in the range of 0.15 to 0.6 mm, and suitably in the range of 0.2 to 0.5 mm. A second set of openings can have a second diameter larger than said first diameter. The second diameter is conveniently in the range of 0.4 to 1.3 mm, such as in the range of 0.7 to 1.2 mm.

In some embodiments the tablet granulating system further comprises a drying device. Powder sweetener or talk may be added to the granules in a final drying step. The drying device can be a conventional centrifugal dryer or another suitable dryer e.g. a fluid bed dryer. The drying device can, for example, include a mixer. The powder sweetener may in an embodiment be sorbitol, which is mixed to the dried or partially dried granules. Minor amounts of residual moisture on the surface of the granules, e.g. 2% Wt. based on the total weight of the granules, may contribute to the adherence of the sorbitol powder to the surface of the granules. It is possible to use a conventional anti-agglomerating agent as e.g. talc, but sorbitol powder can function as an anti-agglomerating agent, and at the same time serves as sweetener. Although sorbitol is found to be most suitable, other bulk sweeteners based on polyols may also be suitable, e.g. mannitol, xylitol, hexa-resorcinol, maltitol, isomalt, erythriol, and lactitol.

In one embodiment the tablet granulating system according to the invention further comprises one or more sieves adapted for removing granules with an average diameter such as above 1.3 mm. The removal of larger granules improves a subsequent tabletting process.

According to an embodiment of the invention at least the extruder and/or the die device comprises means for controlling the temperature of the tablet composition. The means for controlling temperature can be cooling or heating devices, and may serve to facilitate the flow of tablet composition through the extruder and the die device. In an embodiment the extruder comprises delivering means for delivering sweetener and/or flavour to the tablet composition in the extruder.

During extrusion of the tablet composition the differential pressure between the tablet composition in the extruder and the tablet composition in the liquid filled chamber, i.e. over the die device is suitably above 10 bar, such as above 18 bar, such as in the range of 25 to 90 bar. The temperature of the tablet composition in the extruder may for example be in the range of 40 to 125° C., suitably in the range 50 to 115° C. The temperature of the die device may for example be in the range of 60 to 250° C., suitably in the range 80 to 180° C. The temperature of the liquid in the liquid filled chamber is conveniently in the range of 8 to 40° C. The optimum for the pressures and temperatures in the method according to the invention may, however, may be determined by the skilled person as a matter of routine. The optimum values for specific tablet compositions, varies of course, depending on the composition.

The quick cooling in the air filled or water-filled chamber may act to preserve possible fragile ingredients in the tablet composition so that their qualities are better kept intact and conveyed into the granules included in the final tablet product. This improved quality of the tablet composition in the granules improves the general composition of the tablet.

Granule fractions of different average weights may be produced with two different setups, each producing a batch of granules of a particular average weight, followed by a blending of the fractions. It is also possible to design a die means with die openings of at least two different sizes to simultaneously obtain granules with different average diameter. Thus it is possible to obtain granules having different weights. More than two different average weights may be obtained, depending on the design of the die means in use. It is for instance possible to obtain granules with three, four or more different average weights.

The granules may be cut in a very large liquid-filled chamber, in which the granules are also cooled. In some embodiments the cooling is combined with transfer of the granules away from the chamber. This can be done e.g. by cooling the cut granules in water during transfer from the liquid filled chamber to a de-watering device. The transfer time from cutting to de-watering can be less than 6 s. The advantage of this is that water-soluble ingredients in the tablet composition are not unnecessarily washed out of the granules. Optionally, the total time of contact between granules and cooling water can be further limited to less than 4 s.

The inventive tablet may be formed by pressed particles and/or granules. When these are tableted, bonds are established between the particles or granules, thereby conferring a certain mechanical strength to the tablet. Of the particles/granules, the tablet comprises calcium carbonate in an amount of more than 30% by weight of the tablet.

When pressure is applied to the particles/granules, the bulk volume is reduced and the amount of air is decreased. During this process energy is consumed. As the particles/granules come into closer proximity to each other during the volume reduction process, bonds may be established between the particles or granules. The formation of bonds is associated with a reduction in the energy of the system as energy is released.

Volume reduction takes place by various mechanisms and different types of bonds may be established between the particles or granules depending on the pressure applied and the properties of the particles or granules.

Examples of organic water-insoluble components applicable for tablets of the present invention are described in the PCT/DK02/00461 and PCT/DK02/00462, hereby incorporated by reference.

The composition of organic water-insoluble components, which are admixed with tablet ingredients as defined below, can vary substantially depending on the particular product to be prepared and on the desired masticatory and other sensory characteristics of the final product. However, typical ranges (weight %) of the above organic water-insoluble components are: elastomer in the range of 1-15% by weight of the tablet, natural and/or synthetic resin in the range of 5-35% by weight of the tablet, and further other organic water insoluble components in the range of 5-30% by weight of the tablet.

It is evident, that the overall total amount of these above organic water-insoluble components must be mutually adjusted in order to fit requirements with respect to tablet content of calcium carbonate, sweetener, flavor, etc.

Granulates of organic water-insoluble components may be manufactured according to conventional methods or e.g. those described in the PCT/DK02/00461 and PCT/DK02/00462, hereby incorporated by reference.

The following non-limiting examples illustrate different variations of the present invention. The examples are meant for indicating the inventive concept; hence the mentioned examples should not be understood as exhaustive for the present invention.

EXAMPLES

Examples 1-7

Seven different samples, given samples numbers 101-107, of complexes of water insoluble organic compounds are provided in Examples 1-7. The compositions are given in table 1 and the samples were prepared by the following process:

Elastomers and about ⅓ of the resin are mixed at 120° C. together with filler in a pre-heated mixer having horizontally placed Z-shaped arms for mixing. The fillers are talc or non-DC calcium carbonate. The mechanical action of the mixer causes shearing and grinding resulting in softening of the elastomers.

When the elastomers are softened, more resin is slowly added to the elastomer, resin and filler until the mixture becomes homogeneous. The remaining resin is then added to the mixer and mixed for 10-20 minutes. The softeners, i.e. emulsifier, wax and vegetable fat, are then added and mixed for 20-40 minutes until the whole mixture becomes homogeneous.

After a total mixing time of about 45-60 minutes, the mixture is subjected to pelletizing in a standard under water pelletizing (UWP) unit resulting in coherent granules with an average diameter of approximately 1 mm.

The applied polyisobutylene may eg. be Oppanol B12, polyvinyl acetate (PVAc) may eg. be Vinnapas B 1.5 sp, VA-VL copolymers (vinyl acetate—vinyl laurate copolymers) may eg. be Vinnapas B 500/20 VL, natural resin may eg. be Staybelite 5E or Piccolyte C85, softener may eg. be hydrogenated vegetable fat such as hydrogenated sunflower oil, Bulk sweetener may eg. be sorbitol, flavor may eg. be menthol crystals. It is stressed that the specifically mentioned components are of course a non-limiting disclosure intended to assist a skilled person in reproducing the present invention.

In case of Example 7 (sample no. 107), the homogeneous mixture is not subjected to pelletizing but merely discharged into a pan and allowed to cool to room temperature.

Then the mixture is added to another mixer having horizontally placed Z-shaped arms for mixing operating at a temperature of about 40° C. Bulk sweetener is added and mixed until a homogenous mass is obtained.

The mass is discharged and cooled by liquid nitrogen before being introduced to a milling device, in which the mass is milled to obtain particulate material that is ready for tableting.

TABLE 1

Numbers are given in percent by weight of the tablet

| | Raw material Sample no. | Ex. 1 101 | Ex. 2 102 | Ex. 3 103 | Ex. 4 104 | Ex. 5 105 | Ex. 6 106 | Ex. 7 107 |
|---|---|---|---|---|---|---|---|---|
| Organic water insoluble components | Elastomers (butyl rubber and polyisobutylene) | 18 | 21 | 21 | 10 | 10 | 5 | 16 |
| | Resins (polyvinyl acetate (PVAc), VA-VL copolymers and natural resins (ester gums and terpene resins) | 38 | 44 | 44 | 50 | 50 | 55 | 31 |
| | Softeners (wax, fats, emulsifiers) | 23 | 21 | 21 | 22 | 23 | 20 | 19 |
| | Filler (talc) | 18 | 11 | | | 17 | 20 | 14 |
| | Filler (Calcium carbonate) | | | 12 | 15 | | | |
| | Bulk sweetener | | | | | | | 20 |
| | Flavor | 3 | 3 | 2 | 3 | | | |
| | Total | 100 | 100 | 100 | 100 | 100 | 100 | 100 |

Example 8-14

Preparation of Tablets

Tablets, given sample numbers 1001-1007, using the compounds as provided in Examples 1-7, respectively, were prepared as follows:

The compounds of Examples 1-7 are present in the form of particles/granules.

The particulate compounds of Examples 1-7, further tablet compounds and the DC-calcium carbonate are weighed into the proper amounts according to the exampled compositions of table 2.

The weighed amounts are then added to a Turbula mixer in a stainless steel container and blended at 50 rpm for 4 minutes and then adding magnesium stearate and blending one additional minute.

The mixtures are then tableted by means of a Piccola RIVA DC-SC-041-2. A Fette 3090i may also applied.

The resulting tablets according to Examples 8-14 are then obtained by tableting with a suitable pressure force at about 28-30 kN as main compression force. The tablet weight is 1.8 g for all samples.

The applied bulk sweetener may e.g. be isomalt, high intensity sweetener may eg. be sucralose, flavor may e.g. be spearmint in powder form. Also here, it is stressed that the specifically mentioned components are of course a non-limiting disclosure intended to assist a skilled person in reproducing the present invention.

TABLE 2

Number are given in percent by weight of the tablet

| Raw material Sample no. | Ex. 8 1001 | Ex. 9 1002 | Ex. 10 1003 | Ex. 11 1004 | Ex. 12 1005 | Ex. 13 1006 | Ex. 14 1007 |
|---|---|---|---|---|---|---|---|
| Sample 101 (Ex. 1) | 30 | | 15 | | | | |
| Sample 102 (Ex. 2) | | 33 | 18 | | | | |
| Sample 104 (Ex. 4) | | | | 40 | | | |
| Sample 105 (Ex. 5) | | | | | 45 | | |
| Sample 106 (Ex. 6) | | | | 33 | | | |
| Sample 107 (Ex. 7) | | | | | 40 | | |
| Calcium carbonate DC | 35 | 45 | 45 | 45 | 45 | 30 | 16 |
| Bulk sweetener | 32 | 19 | 19 | 19 | 12 | 27 | 36 |
| High intensity sweetener | 0.5 | 0.5 | 0.5 | 0.5 | 0.5 | 0.5 | 0.5 |
| Flavor | 2 | 2 | 2 | 2 | 2 | 2 | 2 |
| Mg stearate | 0.5 | 0.5 | 0.5 | 0.5 | 0.5 | 0.5 | 0.5 |
| Total | 100 | 100 | 100 | 100 | 100 | 100 | 100 |

Example 15

In Vitro Release of Calcium Carbonate from Tablets

The release of calcium carbonate in this example was determined in vitro. The measurements were carried out according to the procedure set forth in the Ph. Eur. 6th ed. 2.9.25, in a phosphate buffer with pH=7.4, a mastication rate of 60 chew per minute, and with the temperature of the medium set at 37° C. The mastication process was interrupted every minute to replace the phosphate buffer thereby preventing saturation of the buffer and simulating swallowing in the in vivo mastication process.

For each sample one tablet was masticated at specified time intervals 3, 5 and 10 minutes to produce tablet residuals for each time point. This was repeated 6 times to obtain 6 replicates for each time point in the test.

Calcium carbonate content of the residuals after mastication was determined by standard Atomic absorption spectroscopy (AAS). For analysis, a tablet residual was dissolved in a mixture of hydrochloric acid (HCl) and toluene. Following proper dilution and filtration, the acidic phase was passed through the AAS device analyzing for Ca (at a wave length of 442.7 nm).

The release was then calculated by comparing the Ca content of the residual after mastication with the Ca content of the non-masticated tablet.

Alternatively, standard titration techniques may be used to determine the calcium carbonate content before and after mastication.

Results (averages of replicate results)

| Release % | 0 min | 3 min | 5 min | 10 min |
|---|---|---|---|---|
| 1001 (Ex. 8) | 0 | 62 | 81 | 86 |
| 1002 (Ex. 9) | 0 | 70 | 91 | 95 |

Example 16

Assessment of Teeth Cleaning Capability of Samples 1001 (Ex. 8) and 1002 (Ex. 9)

A test panel of 8 persons trained for sensory evaluation was used. The trained persons were instructed not to eat or drink anything but water for the last 30 minutes before the test. The test panel was instructed to masticate the samples at a rate of 60 chews per minute for a total mastication time of 10 minutes.

Besides evaluation of standard sensory attributes such as softness and taste intensity the trained persons were instructed to assess the teeth cleaning capability of the samples by answering the question: "Is any tablet residue left in the teeth?" (yes/no) at distinct time points during the mastication process.

The results of this assessment are provided in tables 3 and 4 below

TABLE 3

| assessment of teeth cleaning capability | | | | | | | |
|---|---|---|---|---|---|---|---|
| 1001 (Ex. 8) | 0 min | ½ min | 1 min | 2 min | 3 min | 5 min | 10 min |
| Assessor 1 | N/A | No | No | No | No | No | No |
| Assessor 2 | N/A | No | No | No | No | No | No |
| Assessor 3 | N/A | No | No | No | No | No | No |
| Assessor 4 | N/A | No | No | No | No | No | No |
| Assessor 5 | N/A | No | No | No | No | No | No |
| Assessor 6 | N/A | No | No | No | No | No | No |
| Assessor 7 | N/A | No | No | No | No | No | No |
| Assessor 8 | N/A | No | No | No | No | No | No |

TABLE 4

| assessment of teeth cleaning capability | | | | | | | |
|---|---|---|---|---|---|---|---|
| 1002 (Ex. 9) | 0 min | ½ min | 1 min | 2 min | 3 min | 5 min | 10 min |
| Assessor 1 | N/A | No | No | No | No | No | No |
| Assessor 2 | N/A | No | No | No | No | No | No |
| Assessor 3 | N/A | No | No | No | No | No | No |
| Assessor 4 | N/A | No | No | No | No | No | No |
| Assessor 5 | N/A | No | No | No | No | No | No |
| Assessor 6 | N/A | No | No | No | No | No | No |
| Assessor 7 | N/A | No | No | No | No | No | No |
| Assessor 8 | N/A | No | No | No | No | No | No |

Example 17

Assessment of Chalkiness, Ie. Calcium Carbonate Residue of Samples 1001 (Ex. 8) and 1002 (Ex. 9)

A test panel of 8 persons trained for sensory evaluation was used. The trained persons were instructed not to eat or drink anything but water for the last 30 minutes before the test. The test panel was instructed to masticate the samples at a rate of 60 chews per minute for a total mastication time of 5 minutes.

Besides evaluation of standard sensory attributes such as softness and taste intensity the trained persons were in this test instructed to assess chalkiness, ie the feeling of calcium carbonate residue in the oral cavity, by answering the question: "Is any calcium carbonate residue left in the mouth, ie is a chalkiness feeling present?" (yes/no) at distinct time points during the mastication process.

The results of this assessment are provided in tables 5 and 6 below

TABLE 5

| assessment of chalkiness | | | | | |
|---|---|---|---|---|---|
| 1001 (Ex. 8) | 0 min | 1 min | 2 min | 3 min | 5 min |
| Assessor 1 | N/A | No | No | No | No |
| Assessor 2 | N/A | No | No | No | No |
| Assessor 3 | N/A | No | No | No | No |
| Assessor 4 | N/A | No | No | No | No |
| Assessor 5 | N/A | No | No | No | No |
| Assessor 6 | N/A | No | No | No | No |
| Assessor 7 | N/A | No | No | No | No |
| Assessor 8 | N/A | No | No | No | No |

TABLE 6

| assessment of chalkiness | | | | | |
|---|---|---|---|---|---|
| 1002 (Ex. 9) | 0 min | 1 min | 2 min | 3 min | 5 min |
| Assessor 1 | N/A | No | No | No | No |
| Assessor 2 | N/A | No | No | No | No |
| Assessor 3 | N/A | No | No | No | No |
| Assessor 4 | N/A | No | No | No | No |
| Assessor 5 | N/A | No | No | No | No |
| Assessor 6 | N/A | No | No | No | No |
| Assessor 7 | N/A | No | No | No | No |
| Assessor 8 | N/A | No | No | No | No |

What is claimed is:

1. A solid pharmaceutical tablet for oral delivery, the tablet comprising calcium carbonate and organic water-insoluble components in a calcium carbonate to organic water-insoluble components weight ratio of at least 0.6, wherein the tablet is designed to be masticated into a coherent residual containing the organic water-insoluble components, and wherein the tablet is adapted to release more than 80% of the calcium carbonate within 5 minutes of mastication, wherein the tablet comprises calcium carbonate in an amount of more than 15% by weight of the tablet, wherein the tablet comprises bulk sweetener in an amount of at least 5% by weight of the tablet, wherein the tablet is composed of a pressed mixture of particles and/or granules, and wherein more than 80% of the calcium carbonate is contained in particles and/or granules different from the particles and/or granules comprising the organic water-insoluble components before tableting.

2. The tablet according to claim 1, wherein the calcium carbonate to organic water-insoluble components weight ratio is at least 0.9.

3. The tablet according to claim 1, wherein the calcium carbonate to organic water-insoluble components weight ratio is at least 1.3.

4. The tablet according to claim 1, wherein the calcium carbonate to organic water-insoluble components weight ratio is at least 1.4.

5. The tablet according to claim 1, wherein the tablet comprises organic water-insoluble components in an amount of more than 11% by weight of the tablet.

6. The tablet according to claim 1, wherein the tablet comprises organic water-insoluble components in an amount of 11 to 50% by weight of the tablet.

7. The tablet according to claim 1, wherein the tablet comprises calcium carbonate in an amount of more than 15% and up to 60% by weight of the tablet.

8. The tablet according to claim 1, wherein the organic water-insoluble components comprise elastomer in a range of 1-15% by weight of the tablet.

9. The tablet according to claim 1, wherein the organic water-insoluble components comprise natural and/or synthetic resin in a range of 5-35% by weight of the tablet.

10. The tablet according to claim 1, wherein the organic water-insoluble components comprise further other organic water insoluble components in a range of 5-30% by weight of the tablet.

11. The tablet according to claim 1, wherein the tablet comprises bulk sweetener in an amount of between 5 to 70% by weight of the tablet.

12. The tablet according to claim 1, wherein the tablet comprises bulk sweetener in an amount of between 20 to 70% by weight of the tablet.

13. The tablet according to claim 1, wherein bulk sweetener is selected from sugar sweetener and sugar alcohol sweeteners.

14. The tablet according to claim 13, wherein calcium carbonate and the organic water-insoluble components are contained in different particles and/or granules before tableting.

15. The tablet according to claim 1, wherein bulk sweetener comprises at least one sugar alcohol sweetener selected from sorbitol, mannitol, xylitol, maltitol, isomalt, erythritol, and lactitol.

16. The tablet according to claim 1, wherein the tablet comprises a further active pharmaceutical ingredient.

17. The tablet according to claim 16, wherein the further active pharmaceutical ingredient is an ingredient that provides a gastrointestinal benefit.

18. The tablet according to claim 16, wherein the further active pharmaceutical ingredient comprises an antacid.

19. A solid pharmaceutical tablet for oral delivery, the tablet comprising calcium carbonate and organic water-insoluble components in a calcium carbonate to organic water-insoluble components weight ratio of at least 0.6, wherein the tablet is designed to be masticated into a coherent residual containing the organic water-insoluble components, wherein the tablet is adapted to release more than 80% of the calcium carbonate within 5 minutes of mastication, and wherein the tablet comprises bulk sweetener in an amount of at least 5% by weight of the tablet.

20. A solid pharmaceutical tablet for oral delivery, the tablet comprising calcium carbonate and organic water-insoluble components in a calcium carbonate to organic water-insoluble components weight ratio of at least 0.9, wherein the tablet is designed to be masticated into a coherent residual containing the organic water-insoluble components, and wherein the tablet comprises bulk sweetener in an amount of at least 5% by weight of the tablet,
wherein the tablet is composed of a pressed mixture of particles and/or granules, and wherein more than 80% of the calcium carbonate is contained in particles and/or granules different from the particles and/or granules comprising the organic water-insoluble components before tableting.

* * * * *